US00PP10779P

United States Patent [19]

Austin

[11] Patent Number: Plant 10,779

[45] Date of Patent: Feb. 9, 1999

[54] SHRUB ROSE PLANT NAMED 'AUSWAY'

[75] Inventor: David Charles Henshaw Austin, Albrighton, England

[73] Assignee: David Austin Roses Limited, Albrighton, England

[21] Appl. No.: 788,553

[22] Filed: Jan. 24, 1997

[51] Int. Cl.[6] ..... A01H 5/00

[52] U.S. Cl. ..... Plt./1

[58] Field of Search ..... Plt./1, 22, 11

*Primary Examiner*—Howard J. Locker

*Attorney, Agent, or Firm*—Klarquist Sparkman Campbell Leigh & Whinston, LLP

[57] ABSTRACT

A new and distinct variety of shrub rose plant having a unique combination of beautifully full flowers with petals arranged in perfect formation; flowers of deep magenta crimson; short, upright growth; strong fragrance; and resistance to disease.

1 Drawing Sheet

The present invention relates to a new and distinct variety of shrub rose plant of the rosa hybrida class which was originated by me by crossing unnamed seedlings. The primary objective of this breeding was to produce a new shrub rose variety having repeat flowering with old fashioned flowers of a crimson color. The objective was substantially achieved, along with other desirable improvements, as evidenced by the following unique combination of characteristics that are outstanding in the new variety and that distinguish it from its parents, as well as from all other varieties of which I am aware:

1. Beautifully full flowers;
2. Petals arranged in perfect formation;
3. Flowers of a beautiful, deep magenta crimson;
4. Short, upright growth;
5. Strong fragrance; and
6. Disease resistance.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—Rosa hybrida.

*Commercial.*—Shrub.

Flower

Observations made from specimens grown in a garden environment at Albrighton, Wolverhampton, England in July 1993.

Blooming habit: Recurrent.

Bud:

*Size.*—About 1.3 inches long when the petals start to unfurl.

*Form.*—The bud form is short, blunt topped, broad based.

*Color.*—When sepals first divide, bud color is Red-Purple Group 60A. When half brown, the upper sides of the outer petals are Red-Purple Group 67A and of the inner petals are Red-Purple Group 66A; and the lower sides of the petals are Red-Purple Group 67C.

*Sepals.*—Color: Yellow-Group 144A with an overlying blush of Greyed-Purple Group 184B. Surface texture: Smooth. There are three lightly appendaged sepals. There are two unappendaged sepals with hairy edges.

*Receptacle.*—Color: Yellow-Green Group 144B/C with an overlying blush of Greyed-Purple Group 184B. Shape: Funnel, wide cup. Size: Medium, broad (about 0.3 inches×0.6 inches). Surface: Smooth.

*Peduncle.*—Length: Short (about 1.3 inches). Surface: Glandular. Color: Light green, bronzy. Strength: Stiff, erect, heavy.

Bloom:

*Size.*—Large to medium. Average open size is about 3.5 inches.

*Borne.*—Singly and several together in clusters of irregular shape of up to five blossoms.

*Stems.*—Medium, strong.

*Form.*—When first open: High centered. Permanence: Flattens slightly, all petals curl, the outer petals roll back on fully open bloom.

*Petalage.*—Number of petals under normal conditions: 85 to 90.

*Color.*—The upper sides of the petals are Red-Purple Group 66A. The reverse sides of the petals are Red-Purple Group 67B/C, the middle of the under side of the outer petals paling to Red-Purple Group 65C at the lightest to Red-Purple Group 65A. The base of each petal has a small yellow tip of Yello Group 5A. The major color on the upper sides is Red-Purple Group 66A.

*Variegations.*—None.

*Discoloration.*—The general tonality at the end of the first day: Paler (Red-Purple Group 67C). At the end of the third day: Paler, more Purple, less Red-Purple Group 67C/D.

*Fragrance.*—Moderate to strong, very sweet.

Petals:

*Texture.*—Thin.

*Shape.*—Deltoid; inner narrow with notched apex; outer much broader.

*Form.*—Tips slightly recurved; outer petal edges roll back on fully open bloom.

*Arrangement.*—Imbricated, with few petaloids in the center.

*Persistence.*—Petals drop off cleanly before drying.

*Lastingness.*—On the plant: Fair (about 4–5 days). As a cut flower: Not tested.

Reproductive parts:

*Anthers.*—Size: Medium. Quantity: Many. Color: Yellow. Arrangement: Regular around styles, mixed with petaloids.

*Filaments.*—Color: Yellow.

*Pollen.*—Color: Gold yellow.

*Styles.*—Color: Greenish white, foliate.

*Stigmas.*—Color: Greenish white.

Form: Bush, shrub. Mature plant height about 36 inches, width about 30 inches.

Growth: Vigorous, upright, branching, fairly compact.

Foliage: Number of leaflets on normal mid-stem leaves: 5.

*Size.*—Medium, small (about 5.5 inches long×3.5 inches wide).

*Quantity.*—Abundant to normal.

*Color.*—New foliage: Yellow-Green Group 147A/B with Greyed-Purple Group 183B/C blush on margins. Old foliage: Upper surface: Yellow-Green Group 147A. Lower Surface: Yellow-Green Group 147B.

Leaflets:

*Shape.*—Broadly oval, elliptic and pointed apex.

*Texture.*—Upper side: Leathery, slightly glossy.

*Edge.*—Serrated.

*Serration.*—Doubled, small.

*Petiole rachis.*—Color: Green, reddish.

*Petiole underside.*—With prickles, 1–2 per internode.

*Stipules.*—Medium, short, serrated (about 0.8 inches long).

*Disease resistance.*—Resistant to mildew and blackspot under normal growing conditions at Albrighton, Wolverhampton, England.

Wood:

*New wood.*—Color: Reddish, medium green. Bark: Smooth between prickles.

*Old wood.*—Color: Green, reddish brown blotches, streaky. Bark: Fairly rough.

Prickles:

*Quantity.*—On main canes from base: Many to ordinary. On laterals from main canes: Many to ordinary.

*Form.*—Medium, straight (T-shaped, i.e., wide base to narrow spike).

*Color when young.*—Red, transparent.

*Position.*—Evenly distributed around stem.

Small Prickles:

*Quantity.*—On main stalks: Many. On laterals: Many.

*Color.*—Brown on old stems, transparent red on young stems.

I claim:

1. A new and distinct variety of shrub rose plant of the rosa hybrida class, substantially as herein shown and described, characterized particularly as to novelty by the unique combination of its beautifully full flowers with petals arranged in perfect formation; flowers of deep magenta crimson; short, upright growth; strong fragrance; and resistance to disease.

* * * * *

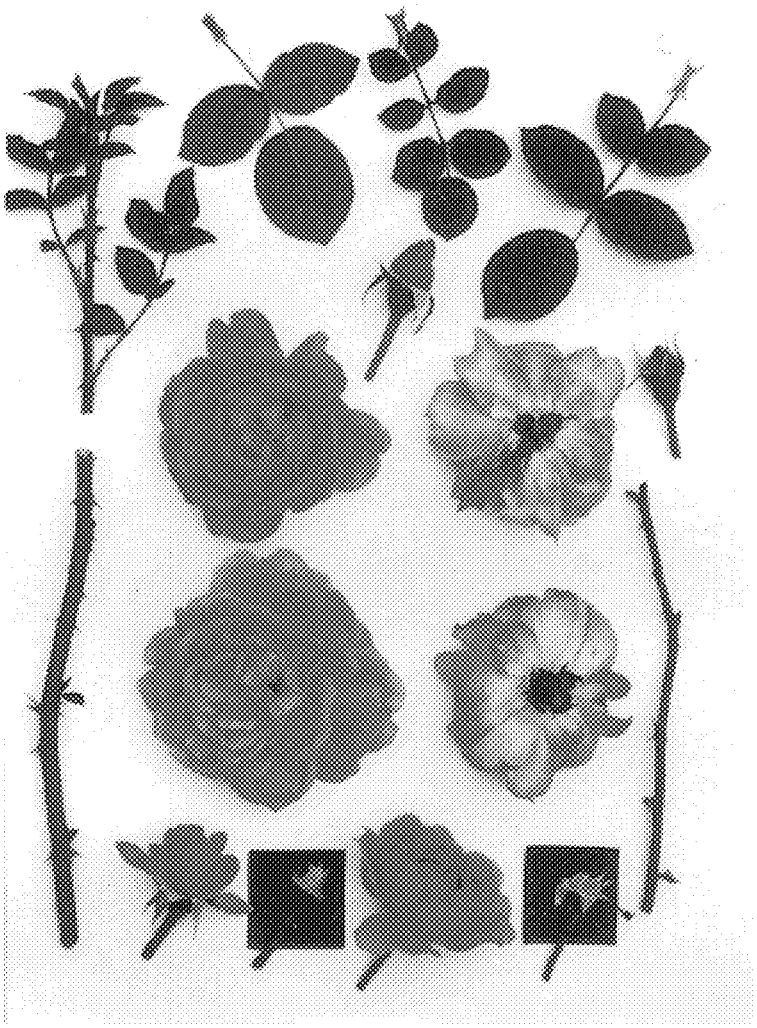

UNITED STATES PATENT AND TRADEMARK OFFICE

CERTIFICATE OF CORRECTION

PATENT NO. : Plant 10,779

DATED : February 9, 1999

INVENTOR(S) : David Charles Henshaw Austin

It is certified that error appears in the above-indentified patent and that said Letters Patent is hereby corrected as shown below:

Column 1/Line 28, change "cultivar color" to --cultivar with color--.

Column 3/Line 25, after "foliage:" insert --Upper surface:--.

Signed and Sealed this

Tenth Day of April, 2001

*Attest:*

Nicholas P. Godici

NICHOLAS P. GODICI

*Attesting Officer*

*Acting Director of the United States Patent and Trademark Office*